United States Patent [19]
Nobuto et al.
[11] Patent Number: 4,484,817
[45] Date of Patent: Nov. 27, 1984

[54] COLORIMETRIC CHEMICAL ANALYZING APPARATUS

[75] Inventors: Toru Nobuto; Asao Hayashi; Koji Kambara; Hitomi Tojiki; Nagahiro Gocho, all of Hachioji, Japan

[73] Assignee: Olympus Optical Co., Ltd., Tokyo, Japan

[21] Appl. No.: 395,630

[22] Filed: Jul. 6, 1982

[30] Foreign Application Priority Data

Jul. 8, 1981 [JP] Japan ................................ 56-105647

[51] Int. Cl.$^{3}$ ................................................ G01J 3/50
[52] U.S. Cl. ..................................... 356/416; 356/419
[58] Field of Search ............... 356/402, 407, 409, 414, 356/416, 419; 250/226

[56] References Cited

U.S. PATENT DOCUMENTS 3,869,212 3/1975 Burcher et al. ..................... 356/419
4,054,389 10/1977 Owen .................................. 356/419

*Primary Examiner*—F. L. Evans
*Attorney, Agent, or Firm*—Parkhurst & Oliff

[57] ABSTRACT

In a chemical analyzing apparatus of a colorimetric type in which a light flux transmitted through a test liquid is made incident upon a light receiving element through an optical filter having a predetermined transmission spectrum range and a measurement signal is obtained by processing a photoelectrically converted signal, a plurality of optical filters having different transmission spectrum ranges and arranged side by side and a solid state image sensor having a plurality of light receiving elements each having a photoelectric converting element and a static induction transistor are arranged one upon the other. An analytical result is obtained by calculating output signals selectively derived from light receiving elements which are arranged behind a particular optical filter having a transmission spectrum range related to a wavelength determined by a test item to be studied. Since use is made of a static induction transistor, it is not necessary to change the optical filters mechanically and is possible to read out the necessary output signals having high S/N selectively in a prompt manner, while the levels of output signals can be monitored.

17 Claims, 7 Drawing Figures

21
25
24
17-1
17-4
23
19
16-4
16-1
26
M
20
M
28
Random Access Memory
31
29
Center Processing Unit
30
Operation Unit
Motor Control Circuit
27
Motor Control Circuit PRIOR ART
FIG_1
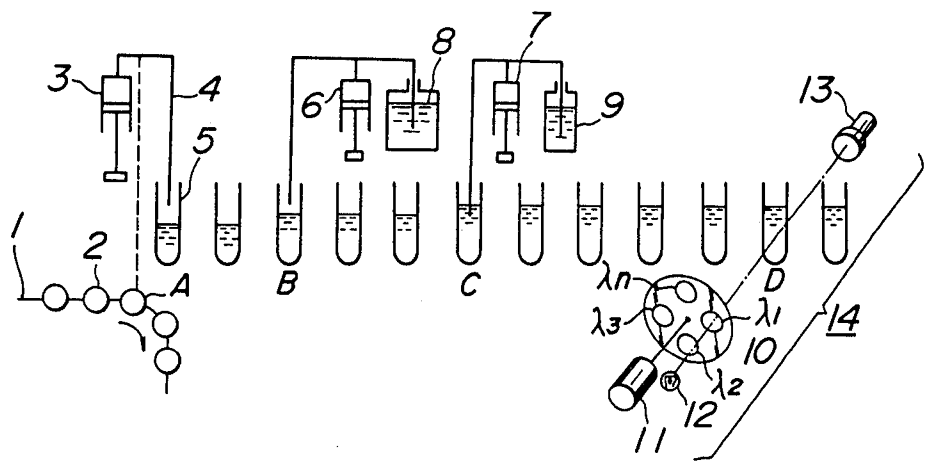
FIG_2A
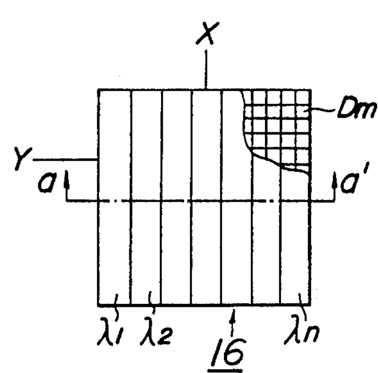
FIG_2B
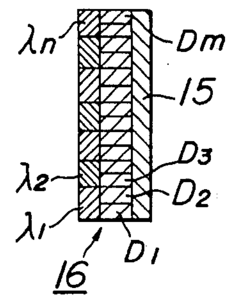
FIG_3
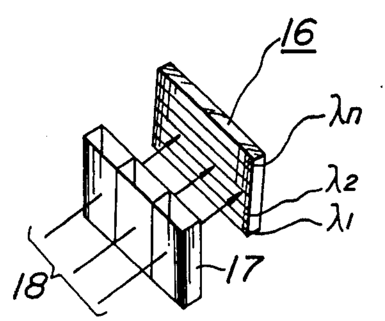
FIG_4
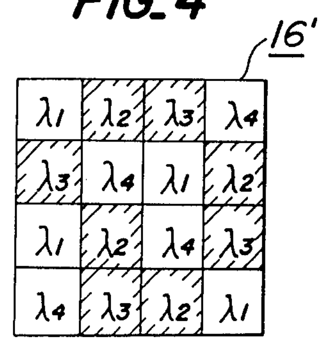

FIG_5
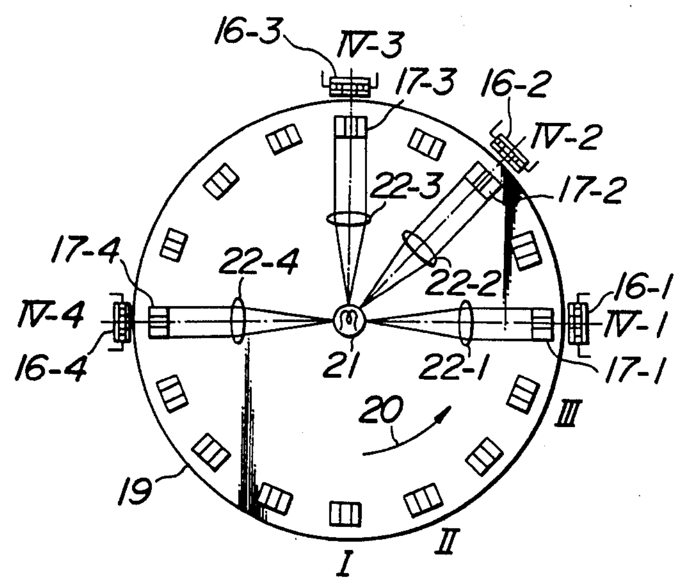
FIG_6
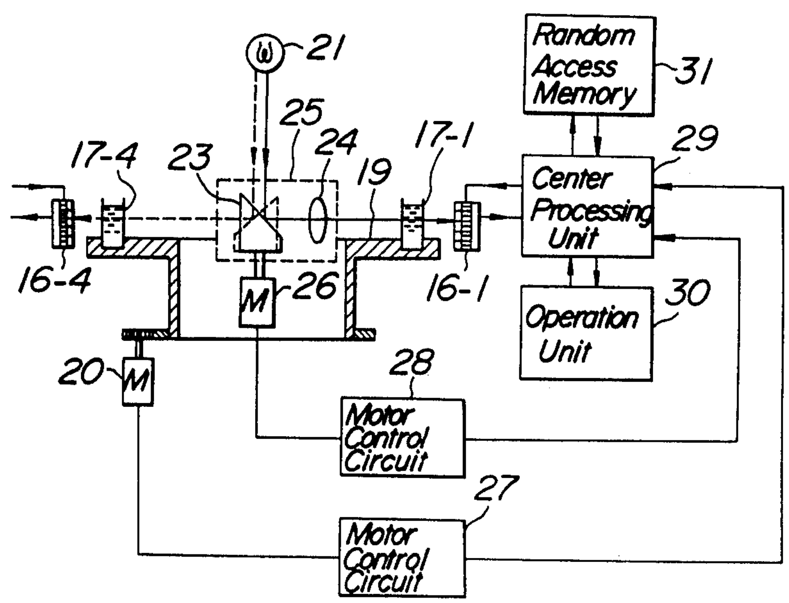

COLORIMETRIC CHEMICAL ANALYZING APPARATUS

BACKGROUND OF THE INVENTION

The present invention relates to a chemical analyzing apparatus, and more particularly to a colorimetric photometering apparatus utilizing a plurality of optical filters having different transmission spectrum ranges.

FIG. 1 is a schematic view showing an outline of a known photoelectric colorimetering analyzer. In FIG. 1, sample vessels 2 are transported successively into a position A by means of a snake chain 1 and a given amount of a sample contained in a sample vessel 2 situated at the position A is sucked into a nozzle 4 of a syringe 3. Then, the sucked sample is delivered into a reaction vessel 5. While the reaction vessel 5 is transported along a reaction line, at positions B and C, a first reagent 8 and a second reagent 9 are delivered into the reaction vessel 5 by syringes 6 and 8, respectively to form a test liquid. When the reaction vessel 5 reaches a position D, the test solution in the reaction vessel 5 is photometered photoelectrically by a colorimeter 14 comprising a rotary disc 10 for holding a plurality of optical filters $\lambda_1$, $\lambda_2$, . . . , $\lambda n$ along its periphery, a stepping motor 11 for rotating the disc 10, a light source 12, and a photoelectric converting element 13 such as a photomultiplier. The filters $\lambda_1$, $\lambda_2$, . . . , $\lambda n$ have different transmission spectrum ranges corresponding to test items to be effected.

In multi-item colorimetering, usually it is necessary to use a light beam having a spectrum range most suitable for a desired test item and therefore, any desired optical filter must be selected by rotating the disc 10 having a plurality of the optical filters $\lambda_1$, $\lambda_2$, . . . , $\lambda n$ by means of the stepping motor 11.

Disadvantages of the known photoelectric colorimeter mentioned above which is so constructed that the optical filter is selected mechanically are as follows.

(1) Since selection of the optical filter is effected by a mechanically driving mechanism, a relatively long time is required so that the processing time becomes longer.

(2) Since a large size driving mechanism for selecting the optical filter is required, the whole colorimeter is made large in size.

(3) In case of performing a two wavelength photometering which uses two optical filters having different spectrum ranges, since it is necessary to rotate the filter disc twice, a longer time is required than one wavelength photometering.

(4) Since it is necessary to insert the optical filter into an optical path correctly, the driving mechanism needs high precision.

(5) In order to effect a positioning described in (4), it is necessary to make diameters of the optical filters much larger than that necessary, and therefore the number of optical filters arranged on the rotary disc is limited.

SUMMARY OF THE INVENTION

The present invention has for its object to provide a novel and useful chemical analyzing apparatus which can eliminate the drawbacks mentioned above by deleting the necessity of changing the optical filters mechanically.

It is another object of the invention to provide a chemical analyzing apparatus comprising a photoelectric converting device which can produce output signals having excellent linearity and high signal-to-noise ratio.

It is still another object of the invention to provide a chemical analyzing apparatus comprising a photoelectric converting device whose output signals can be monitored in a nondestructive manner.

It is still another object of the invention to provide a chemical analyzing apparatus comprising a photoelectric converting device having a plurality of light receiving elements which can be random-accessed.

According to the invention, a chemical analyzing apparatus for effecting a photometric measurement upon a test solution by projecting a light flux upon the test solution and receiving a light flux transmitted through or scattered by the test solution comprises optical means for projecting a light flux having a given spectrum range upon a test solution;

filter means comprising a plurality of optical filters which have different transmission spectrum ranges within said given spectrum range and are arranged side by side at such a position that at least a part of the light flux transmitted through or scattered by the test solution is passed through the optical filters;

photoelectric converting means comprising at least one solid state image sensor having a plurality of light receiving elements each of which is so arranged to receive a light flux transmitted through a particular optical filter of said filter means to produce an output signal; and signal processing means for selectively processing an output signal produced by at least one light receiving element which receives a light flux transmitted through at least one optical filter having a transmission spectrum range determined by a test item to be analyzed and producing an analytical result.

BRIEF DESCRIPTION OF THE DRAWINGS

FIG. 1 is a schematic view showing an outline of a known photoelectric colorimetering analyzer;

FIGS. 2A and 2B are a plan view and a cross sectional view illustrating one embodiment of an image sensor according to the invention;

FIG. 3 is a perspective view explaining the positional relation between an image sensor and a reaction vessel according to the invention;

FIG. 4 is a schematic view showing another embodiment of the image sensor according to the invention;

FIG. 5 is a schematic view illustrating one embodiment of the chemical analyzing apparatus according to the invention; and FIG. 6 is a schematic view depicting another embodiment of the chemical analyzing apparatus according to the invention.

DESCRIPTION OF THE PREFERRED EMBODIMENTS

FIG. 2A is a plan view, as seen from a light incident side, showing one embodiment of an image sensor 16 according to the invention, and FIG. 2B is a cross sectional view of the same cut along a line a—a' in FIG. 2A. As shown in FIGS. 2A and 2B, on the light incident side, many kinds of stripe-shaped optical filters $\lambda_1$, $\lambda_2$, . . . , $\lambda n$ having different spectral ranges are arranged adjacently one by one. On a rear side of the filters, photoelectric converting elements $D_1$, $D_2$, . . . , $Dm$, each including a light receiving element such as photodiode and phototransistor and a static induction transistor (SIT) are arranged in a matrix form. Hereinafter such a photoelectric converting element is called "SIT element" for the sake of simplicity. It should be noted that since a width of each of the filters $\lambda_1$, $\lambda_2$, . . . , $\lambda n$ is made equal to integer multiples of that of the SIT, element, the SIT elements are arranged to be aligned with the optical filters. The SIT elements $D_1$, $D_2$, . . . , Dm are all formed in a common semiconductor substrate 15 and are directly applied on the rear surface of the filters.

In the present embodiment, the SIT elements $D_1$, $D_2$, . . . , Dm are of rectangular shape, but various alterations in its shape are possible. For example, it is possible to use an elongated SIT element having the same shape as that of the optical filter, and the width of the SIT element may be set to any value as long as it is not intruded into a region of adjacent stripe-shaped optical filters. Moreover, it is possible to arrange any desired number of SIT elements along a width of one optical filter. For example, in the embodiment shown in FIG. 2B, two SIT elements are arranged in the width direction of the optical filter. The image sensor 16 comprising light sensitive elements and static induction transistors is well known in the art and is described in, for instance, "Static Induction Transistor Image Sensors", IEEE Trans. Electron Devices, ED-26, 1979. Such a static induction transistor image sensor has remarkable properties such that random access and nondestructive read out can be performed and the sensitivity is very high, and thus, it may be preferably applied to the present invention.

In the embodiment mentioned above, since the image sensor 16 comprises the SIT elements arranged in a matrix form, a photoelectrically converted output generated from each SIT element can be read out independently corresponding to commands of X, Y addresses.

The image sensor 16 comprising the SIT elements is arranged at the photometry position of the chemical analyzing apparatus in such a manner that a light flux 18 emitted from a light source not shown impinges upon the image sensor 16 through three reaction vessels 17 as shown in FIG. 3. The light flux 18 is passed through the stripe-shaped optical filters $\lambda_1$, $\lambda_2$, . . . , $\lambda n$ after transmitting the reaction vessel 17, and impinges upon light receiving surfaces of the SIT elements arranged closely to a rear surface of the optical filters as shown in FIG. 2B. It should be noted that the image sensor 16 is so arranged with respect to the reaction vessels 17 that the filters extend in a parallel manner with respect to the reaction vessels. This results in each SIT element storing a charge proportional to the intensity of light which is received by the SIT element through the optical filter arranged in front of the relevant SIT element.

According to the present embodiment, since the static induction transistor of the SIT element has a linearity over a very wide range and an amplifying function, it is possible to obtain an output signal having an extremely high signal-to-noise ratio and thus, test results can be obtained in an accurate and reliable manner.

Moreover, since the image sensor 16 comprising the SIT elements can be addressed at random, any desired test item can be selected simply by addressing SIT elements which are arranged behind any desired stripe-shaped optical filter having a transmission spectrum range to be used for the relevant test item. In this manner, desired output signals can be selectively derived from the SIT elements and a test result can be calculated by supplying the output signals thus derived to a known processing circuit.

In case of performing a two wavelength measurement which uses two optical filters having different transmission spectrum ranges, those SIT elements which are arranged behind two optical filters having desired transmission spectrum ranges are selectively addressed to derive necessary information. In this case, since it is not necessary to move the filter member mechanically, the required output signals can be obtained substantially simultaneously with the aid of purely electronic means.

Furthermore, since the output of the SIT element can be read-out nondestructively, it is possible to monitor the output signal, i.e. the reaction progress and therefore, photometry data can be derived at optimum instants, and accurate analysis results can be obtained.

FIG. 4 is a schematic view showing another embodiment of the image sensor 16' according to the invention. In this embodiment, a plurality of optical filters $\lambda_1$, $\lambda_2$, . . . , $\lambda n$ having different transmission spectrum ranges and about $1 \times 1$ mm square shape are arranged in a mosaic manner such that the optical filters having the same transmission spectrum range are not adjacent to each other as shown in FIG. 4, and on a rear surface of each of the optical filters is arranged at least one SIT element. In case of effecting the two wavelength photometry by using the image sensor 16' having the construction mentioned above, SIT elements which are arranged behind particular optical filters, for example filters $\lambda_2$ and $\lambda_3$ as shown by hatched areas in FIG. 4 corresponding to the wavelengths determined by the test item, are selectively addressed to derive output signals. Then these output signals are introduced into a known processing circuit, and an analytical result is obtained from the difference between two average values of the output signals from the SIT elements related to the filters $\lambda_2$ and those related to the filters $\lambda_3$, respectively. In this manner, by deriving the result from the average of output signals from a plurality of SIT elements which are situated behind irregularly arranged filters having the same transmission spectrum range, error which might be caused by unevenness of light source flux and local stains, cracks or scratches of reaction vessels can be effectively removed.

FIG. 5 is a schematic view illustrating one embodiment of the chemical analyzing apparatus according to the invention. In FIG. 5, a turntable 19 is rotated in a counterclockwise direction as shown by arrow 20. At a position I, a set of three cuvettes in which the same or different samples have been delivered is supplied to the turntable 19 and is carried to positions II and III successively at which first and second reagents are delivered respectively. Then, at positions IV-1, IV-2, IV-3, and IV-4, absorbances of the reacted test solutions are photometered and monitored by image sensors 16-1, 16-2, 16-3, and 16-4 arranged at respective positions IV-1 to IV-4. By suitably processing the measured values, rate assay measurement and end point measurement may be effected. To this end, light fluxes emitted from a single light source 21 arranged at the center of the turntable 19 are collimated into parallel light fluxes by respective collimator lenses 22-1, 22-2, 22-3, and 22-4, and these light fluxes are made incident upon the image sensors 16-1, 16-2, 16-3, and 16-4 through the reaction vessels 17-1, 17-2, 17-3, and 17-4, respectively. From each of the image sensors 16-1, 16-2, 16-3, and 16-4, photoelectrically converted output signals corresponding to desired optical filters determined by a given test item are picked up selectively, and are introduced to a processing circuit to derive an analytical result.

FIG. 6 is a schematic view showing a modified embodiment of the analyzing apparatus according to the invention shown in FIG. 5. In FIG. 6, image sensors 16-1 to 16-4 and a turntable 19 are arranged in the same manner as that of the previous embodiment shown in FIG. 5. Reaction vessels 17-1 to 17-4 are placed on the turntable 19. The turntable 19 is rotated by a motor 20 by means of a suitable gear mechanism. A light source 21 emitting light rays covering whole necessary spectrum ranges is arranged above the turntable 19 at the optical axis. A light flux emitted from the light source 21 is introduced into respective image sensors 16-1 to 16-4 through the reaction vessels 17-1 to 17-4 by means of a light deflecting device 25 comprising a rotation mirror 23 and a collimator lens 24. The deflection device 25 is rotated by a motor 26 about the optical axis. The motors 20 and 26 are driven by motor control circuits 27 and 28, respectively. These motor control circuits are connected to a central processing unit 29 to which are also connected the image sensors 17-1 to 17-4. A selection of the image sensors and a read-out of output signals from SIT elements corresponding to a given optical filter having a desired transmission spectrum range related to a desired test item are performed under the control of the center processing unit 29 according to commands from an operation unit 30. The picked-up output signals from the image sensors are stored in a random access memory 31 temporarily so as to effect a required calculation in the center processing unit 29 to derive an analytical result, and then the derived result is indicated by a printer, CRT, etc. arranged in the operation unit 30 under the control of the center processing unit 29.

As mentioned above, according to the invention, since the photometering values corresponding to the test item can be obtained from the image sensor by selectively deriving the output signals of the SIT elements arranged opposite to the optical filter having a transmission spectrum range corresponding to the test item, it is not necessary to provide a driving means for selecting the optical filters mechanically as in the known analyzing apparatus. Therefore, the drawbacks caused by the driving means can be removed completely, the handling of the apparatus becomes easy, and the measuring time period can be made short extremely. Moreover, in the embodiment according to the invention, since the image sensor comprises the SIT elements, it is possible to effect a highly sensitive measurement, to make the apparatus small in size, and to effect a random access for the SIT elements. Furthermore, since a non-destructive read out can be performed, it is possible to monitor the reaction progress from a start point to an end point and thus, the measured values can be derived at optimum timings for effecting the rate assay and end point measurements.

It should be noted that the present invention is not limited to the embodiments explained above, but may be modified in various manners. For instance, use may be made of any other solid state image sensors than the SIT image sensor. Further, the light flux scattered by the test liquid may be equally detected.

What is claimed is:

1. A chemical analyzing apparatus for effecting a photometric measurement upon a test solution by projecting a light flux upon the test solution and receiving a light flux transmitted through or scattered by the test solution, comprising:

(a) optical means for projecting a light flux having a given spectrum range upon a test solution;

(b) filter means comprising a plurality of optical filters which have different transmission spectrum ranges within said given spectrum range, said filters being arranged side by side at such a position that at least a part of the light flux transmitted through or scattered by the test solution is passed through the optical filters;

(c) photoelectric converting means comprising at least one solid state image sensor having a plurality of light receiving elements, each of said light receiving elements being arranged to receive a light flux transmitted through a particular optical filter of said filter means to produce an output signal, wherein each of said light receiving elements comprises a photoelectrically converting element and a static induction transistor coupled to the photoelectrically converting element; and (d) signal processing means for selectively processing an output signal produced by at least one of said light receiving elements and producing an analytical result.

2. An apparatus according to claim 1, wherein said filter means is directly arranged on the photoelectric converting means.

3. An apparatus according to claim 2, wherein all of the optical filters of the filter means have different transmission spectrum ranges.

4. An apparatus according to claim 2, wherein at least two of the optical filters of the filter means have the same transmission spectrum range.

5. An apparatus according to claim 4, wherein the optical filters of the filter means are so arranged that the optical filters having the same transmission spectrum range are not arranged adjacently to each other.

6. An apparatus according to any one of claims 2 to 5, wherein a single light receiving element of the solid state image sensor is arranged behind a single optical filter.

7. An apparatus according to claim 6, wherein said optical filters have a rectangular shape.

8. An apparatus according to claim 6, wherein said optical filters are arranged parallel to each other.

9. An apparatus according to any one of claims 2 to 5, wherein a plurality of light receiving elements of the solid state image sensor are arranged behind each of the optical filters.

10. An apparatus according to claim 9, wherein said optical filters have an rectangular shape.

11. An apparatus according to claim 9, wherein said optical filters are arranged parallel to each other.

12. An apparatus according to claim 9, wherein said signal processing means comprises means for calculating an average of output signals produced by the plurality of light receiving elements which are arranged behind the same optical filter.

13. An apparatus according to claim 1, wherein said filter means and photoelectric converting means have such dimensions as to receive simultaneously the light flux transmitted through or scattered by a plurality of test solutions.

14. An apparatus according to claim 1, wherein a plurality of sets of said photoelectric converting means and filter means are arranged at different positions along a reaction line.

15. An apparatus according to claim 1, wherein said signal processing means comprises means for random-accessing any desired one or more light receiving elements of the solid state image sensor.

16. An apparatus according to claim 1, wherein said optical means comprises a light source for emitting the light flux having the given spectrum range and at least one collimator lens for converting the light flux into a parallel light flux and projecting the parallel light flux upon the test solution.

17. An apparatus according to claim 15, further comprising a reflecting member for reflecting the light flux emitted from the fixedly arranged light source toward the single collimator lens and means for rotating the reflecting member and the collimator lens.

* * * * *